(12) United States Patent
Chopp et al.

(10) Patent No.: US 9,775,883 B2
(45) Date of Patent: Oct. 3, 2017

(54) METHODS, SYSTEMS, AND COMPOSITIONS FOR PROMOTING RECOVERY OF PERIPHERAL NEUROPATHY

(71) Applicant: HENRY FORD HEALTH SYSTEM, Detroit, MI (US)

(72) Inventors: Michael Chopp, Southfield, MI (US); Zhenggang Zhang, Troy, MI (US); Daniel C. Morris, Grosse Point Park, MI (US); Lei Wang, Troy, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 14/367,800

(22) PCT Filed: Dec. 21, 2012

(86) PCT No.: PCT/US2012/071253
§ 371 (c)(1),
(2) Date: Jun. 20, 2014

(87) PCT Pub. No.: WO2013/096773
PCT Pub. Date: Jun. 27, 2013

(65) Prior Publication Data
US 2015/0224175 A1  Aug. 13, 2015

Related U.S. Application Data

(60) Provisional application No. 61/579,951, filed on Dec. 23, 2011.

(51) Int. Cl.
| | | |
|---|---|---|
| *A61K 38/00* | (2006.01) | |
| *A61K 38/28* | (2006.01) | |
| *A61K 38/22* | (2006.01) | |
| *C07K 14/575* | (2006.01) | |

(52) U.S. Cl.
CPC .... *A61K 38/2292* (2013.01); *C07K 14/57581* (2013.01)

(58) Field of Classification Search
None
See application file for complete search history.

(56) References Cited

FOREIGN PATENT DOCUMENTS

| JP | H04234325 A | 8/1992 | | |
|---|---|---|---|---|
| JP | 2009523804 A | 6/2009 | | |
| WO | 00/06190 A1 | 2/2000 | | |
| WO | 2011/057326 A1 | 5/2011 | | |
| WO | WO 2011/057326 | * | 5/2011 | ............ A61K 38/10 |

OTHER PUBLICATIONS

Agrawal et al.: "Prevalence of Micro and Macrovascular Complications and their Risk Factors in Type-2 Diabetes Mellitus", Journal of the Association of Physicians of India, 2014 vol. 62, pp. 504-508.
Azad et al.: "The Effects of Intensive Glycemic Control on Neuropathy in the VA Cooperative Study on Type II Diabetes Mellitus (VA CSDM)", Journal of Diabetes and Its Complications, 1999 vol. 13, pp. 307-313.
Brewer et al.: "Chemotherapy-induced peripheral neuropathy: Current status and progress", Gynecologic Oncology, 2015, pp. 1-8.
Bromberg et al.: "Peripheral Neuropathy in the Nondiabetic Patient", Hospital Practice, 1997, pp. 97-135.
Choi et al. "Neuroprotective function of thymosin-beta and its derivative peptides on the programmed cell death of chick and rat neurons" Biochemical and Biophysical Research Communications, Academic Press Inc., vol. 362, No. 3, 2007, pp. 587-593.
Goldstein et al. "Thymosin beta4: actin-sequestering protein moonlights to repair injured tissues," Trends in Molecular Medicine, Elsevier Current Trends, GB, vol. 11, No. 9, 2005, pp. 421-429.
Ismail-Beigi et al.: "Effect of intensive treatment of hyperglycemia on microvascular complications of type 2 diabetes in Accord: a randomized trial", Lancet, 2010 vol. 376 No. 9739, pp. 419-430.
Kajita et al.: "Increased platelet aggregation in diabetic patients with microangiopathy despite good glycemic control", Platelets, 2001 vol. 12 No. 6, pp. 343-351.
Kannan et al.: "Prevalence of neuropathy in patients with impaired glucose tolerance using various electrophysiological tests", Neurology India, 2014 vol. 62 No. 6, pp. 656-661.
Lei Wang et al. "Thymosin beta4 promotes the recovery of peripheral neuropathy in type II diabetic mice" Neurobiology of Disease, vol. 48, No. 3, 2012, pp. 546-555.
Peng et al.: "Incidence and risk of peripheral neuropathy with nab-paclitaxel in patients with cancer: a meta-analysis", European Journal of Cancer Care, 2015, pp. 1-11.
Wang et al.: "Evaluating peripheral nerve function in asymptomatic patients with type 2 diabetes or latent autoimmune diabetes of adults (LADA): results from nerve conduction studies", Journal of Diabetes and Its Complications, 2015 vol. 29, pp. 265-269.
English translation of Office Action issued in corresponding Japanese Patent Application No. 2014-548952 on Sep. 6, 2016. (7 pages).

* cited by examiner

*Primary Examiner* — Olga N Chernyshev
(74) *Attorney, Agent, or Firm* — Rothwell, Figg, Ernst & Manbeck, P.C.

(57) ABSTRACT

Without limitation, some embodiments comprise a method of treatment for promoting recovery of peripheral neuropathy in a subject, including administering to a subject in need of such treatment a therapeutically effective amount of a composition comprised of thymosin beta 4, amino acid sequences LKKTET or LKKTNT, and/or any conservative variants thereof, or an agent that stimulates production of any of those materials, or a conservative variant thereof.

8 Claims, 7 Drawing Sheets

SEQUENCE LISTING

<160> NUMBER OF SEQ ID NOS: 12

<210> SEQ ID NO 1
<211> LENGTH: 43
<212> TYPE: PRT
<213> ORGANISM: Homo sapiens

<400> SEQUENCE: 1

```
Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
                20                  25                  30

Thr Ile Glu Gln Glu Lys Gln Ala Gly Glu Ser
            35                  40

<210> SEQ ID NO 2
<211> LENGTH: 43
<212> TYPE: PRT
<213> ORGANISM: Homo sapiens
<220> FEATURE:
<221> NAME/KEY: MISC_FEATURE
<223> OTHER INFORMATION: Ac at terminal end before SDK...sequence

<400> SEQUENCE: 2

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
                20                  25                  30

Thr Ile Glu Gln Glu Lys Gln Ala Gly Glu Ser
            35                  40

<210> SEQ ID NO 3
<211> LENGTH: 6
<212> TYPE: PRT
<213> ORGANISM: Homo sapiens

<400> SEQUENCE: 3

Leu Lys Lys Thr Glu Thr
1               5

<210> SEQ ID NO 4
<211> LENGTH: 6
<212> TYPE: PRT
<213> ORGANISM: Homo sapiens

<400> SEQUENCE: 4

Leu Lys Lys Thr Asn Thr
1               5

<210> SEQ ID NO 5
<211> LENGTH: 7
<212> TYPE: PRT
<213> ORGANISM: Homo sapiens

<400> SEQUENCE: 5

Lys Leu Lys Lys Thr Glu Thr
1               5

<210> SEQ ID NO 6
<211> LENGTH: 7
<212> TYPE: PRT
<213> ORGANISM: Homo sapiens

<400> SEQUENCE: 6

Leu Lys Lys Thr Asn Thr Gln
1               5

<210> SEQ ID NO 7
<211> LENGTH: 20
<212> TYPE: DNA
<213> ORGANISM: Artificial Sequence
```

```
<220> FEATURE:
<223> OTHER INFORMATION: Primer

<400> SEQUENCE: 7
agaacatcat ccctgcatcc                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cacattgggg gtaggaacac                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gaagggaacc gagcctattc                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gctgaaatca gcaccgtgta                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cagatccggg ctctagacag                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tccggaaatc gttcttcatc                                              20
```

METHODS, SYSTEMS, AND COMPOSITIONS FOR PROMOTING RECOVERY OF PERIPHERAL NEUROPATHY

CROSS-REFERENCE TO RELATED APPLICATIONS

This application is a 35 U.S.C. §371 National Phase Entry Application from PCT/US2012/071253, filed Dec. 21, 2012, and designating the United States, which claims the benefit of U.S. Provisional Application Ser. No. 61/579,951 filed Dec. 23, 2011, which is incorporated herein in its entirety.

TECHNICAL FIELD

Without limitation, some embodiments relate to the field of promoting recovery of peripheral neuropathy.

BACKGROUND

Peripheral neuropathy is one of the most common and disabling complications of diabetes mellitus. There remains a need in the art for effective methods, systems, and compositions for promoting recovery of peripheral neuropathy.

SUMMARY

The following examples of some embodiments are provided without limiting the invention to only those embodiments described herein and without disclaiming any embodiments or subject matter.

Some embodiments comprise methods of promoting recovery of peripheral neuropathy, comprising administering to a subject in need of such treatment a therapeutically effective amount of a composition comprising a peptide agent comprising amino acid sequence LKKTET or LKKTNT, including but not limited to, thymosin beta 4, conservative variant(s) thereof, or a stimulating agent that stimulates production of an LKKTET (SEQ ID NO: 3) or LKKTNT (SEQ ID NO: 4) peptide, or a conservative variant thereof.

BRIEF DESCRIPTION OF THE DRAWINGS

Some embodiments will now be described, by way of example only and without disclaimer of other embodiments, with reference to the accompanying drawings, in which:

DETAILED DESCRIPTION

Figure 1:
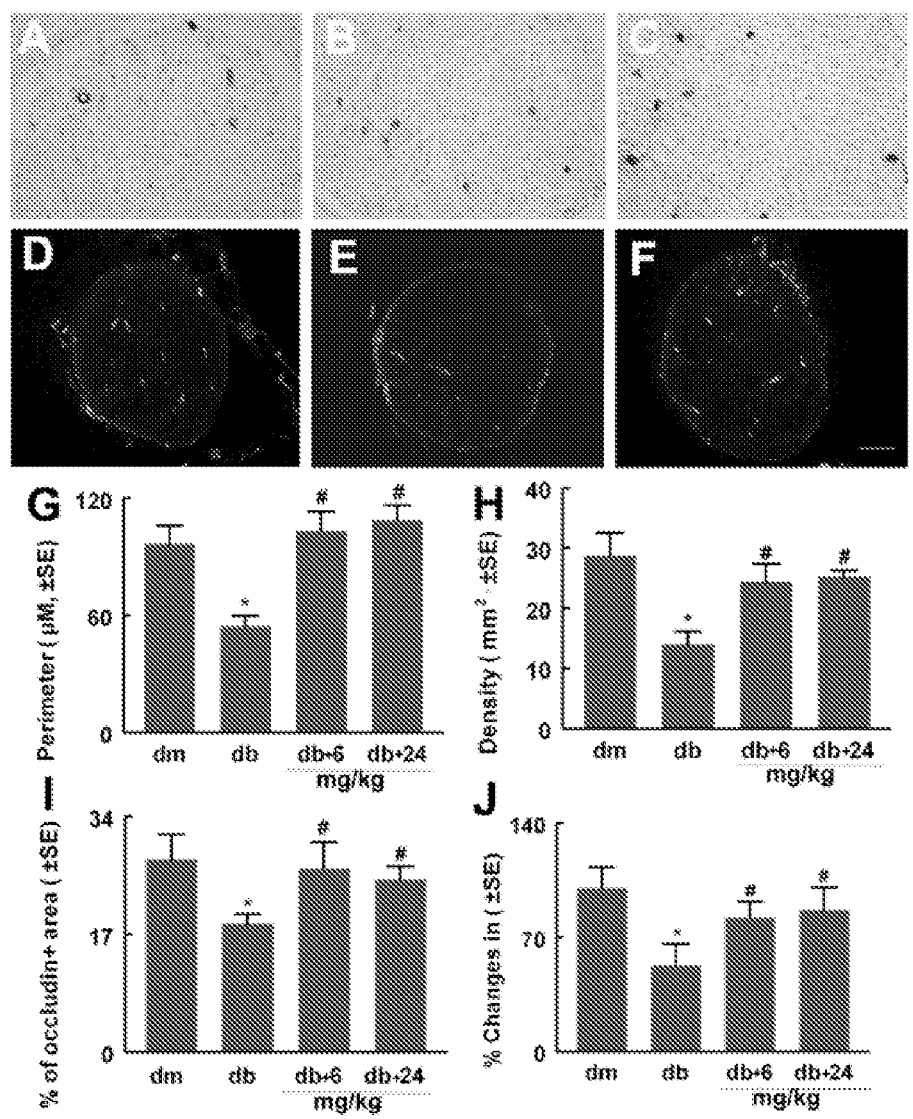
FIG. 1 is images and data representations showing data that indicates that Tβ4 improves vascular function in the sciatic nerve.

Without limitation to only those embodiments expressly disclosed herein and without disclaiming any embodiments or subject matter, and without being bound to any specific theory, some embodiments comprise actin-sequestering peptides such as thymosin beta 4 (also, "Tβ4" or "TB4") and/or other agents comprising actin-sequestering peptides or peptide fragments containing amino acid sequence LKKTET (SEQ ID NO: 3) or LKKTNT (SEQ ID NO: 4), or conservative variants thereof, to promote recovery of peripheral neuropathy in patients suffering therefrom, such as diabetes patients, e.g., type II diabetes, or those suffering from diabetes mellitus.

Thymosin beta 4 was initially identified as a protein that is upregulated during endothelial cell migration and differentiation in vitro. Thymosin beta 4 was originally isolated from the thymus and is a 43 amino acid, 4.9 kDa ubiquitous polypeptide identified in a variety of tissues. (Without limitation, see e.g., SEQ ID NO: 1; some species variation in the precise sequence might exist, and any and all such sequences may comprise some embodiments. In addition, some embodiments may comprise addition of certain chemical groups at one end or both ends of the sequence(s), as one example only and without limitation, SEQ ID NO: 2 listed below). Several roles have been ascribed to this protein including a role in endothelial cell differentiation and migration, T cell differentiation, actin sequestration, vascularization and wound healing.

Some embodiments comprise a method of promoting recovery of peripheral neuropathy, in a subject, comprising administering to a subject in need of such treatment a therapeutically effective amount of a composition comprising a peptide agent, which may be a polypeptide comprising amino acid sequence LKKTET or LKKTNT (respectively, SEQ ID NO: 3 and SEQ ID NO: 4), or a conservative variant thereof, preferably thymosin beta 4, and/or Tβ4 isoforms, analogues or derivatives, including but not limited to, KLK-KTET (SEQ ID NO: 5), LKKTETQ (SEQ ID NO: 6), N-terminal variants of Tβ4, C-terminal variants of Tβ4 and antagonists of Tβ4. Some embodiments also may utilize oxidized Tβ4. In accordance with other embodiments, the agent is other than thymosin beta 4 or other than oxidized Tβ4. In some embodiments, the peptide agent may be a recombinant or synthetic peptide, or an isolated or purified peptide.

Compositions which may be used in accordance with some embodiments include peptide agents such as thymosin beta 4 (Tβ4), and/or Tβ4 isoforms, analogues or derivatives, including oxidized Tβ4, N-terminal variants of Tβ4, C-terminal variants of Tβ4 and antagonists of Tβ4, polypeptides or peptide fragments comprising or consisting essentially of the amino acid sequence LKKTET (SEQ ID NO: 3) or conservative variants thereof. International Application Serial No. PCT/US99/17282, incorporated herein by reference, discloses isoforms of Tβ4 which may be useful in accordance with some embodiments as well as amino acid sequence LKKTET (SEQ ID NO: 3) and conservative variants thereof, which may be utilized with some embodiments. International Application Serial No. PCT/GB99/00833 (WO 99/49883), incorporated herein by reference, discloses oxidized thymosin I34 which may be utilized in accordance with some embodiments. Although some embodiments are described primarily hereinafter with respect to Tβ4 and Tβ4 isoforms, it is to be understood that the following description is intended to be equally applicable to amino acid sequence LKKTET (SEQ ID NO: 3) or LKKTNT (SEQ ID NO: 4), peptides and fragments comprising or consisting essentially of LKKTE (SEQ ID NO: 3)T or LKKTNT (SEQ ID NO: 4), conservative variants thereof having peripheral neuropathy disease-inhibiting activity, and/or Tβ4 isoforms, analogues or derivatives, including N-terminal variants of Tβ4, C-terminal variants of Tβ4 and antagonists of Tβ4. Some embodiments also may utilize oxidized Tβ4.

Some embodiments comprise methods of promoting recovery of peripheral neuropathy in a subject, comprising administering to a subject in need of such treatment a therapeutically effective amount of a composition comprising a peptide agent comprising amino acid sequence LKKTET (SEQ ID NO: 3) or LKKTNT (SEQ ID NO: 4), a conservative variant thereof, or a stimulating agent that stimulates production of an LKKTET (SEQ ID NO: 3) or LKKTNT (SEQ ID NO: 4) peptide, or a conservative variant thereof.

Some embodiments comprise methods of promoting recovery of peripheral neuropathy in a subject, comprising administering to a subject in need of such treatment a therapeutically effective amount of a composition having a peptide agent comprised of amino acid sequence KLKKTET (SEQ ID NO: 5) or, amino acid sequence LKKTETQ (SEQ ID NO: 6), an N-terminal variant of Tβ4, a C-terminal variant of Tβ4, and/or or an isoform of Tβ4.

Some embodiments comprise a method of promoting recovery of peripheral neuropathy, in a subject, by contacting the affected tissue with a therapeutically effective amount of a composition which contains a peptide agent as described herein. Examples of direct administration include, for example, contacting the tissue, by direct application or inhalation, with a solution, lotion, salve, gel, cream, paste, spray, suspension, dispersion, hydrogel, ointment, or oil comprising a peptide agent as described herein. Systemic administration includes, for example, intravenous, intraperitoneal, intramuscular injections of a composition containing a peptide agent as described herein, in a pharmaceutically acceptable carrier such as water for injection.

Peptide agents for use in some embodiments, as described herein, may be administered in any effective amount. For example, a peptide agent as described herein may be administered in dosages within the range of about 0.0001-1,000,000 micrograms, more preferably in amounts within the range of about 0.1-5,000 micrograms, most preferably within the range of about 1-100 micrograms.

A composition in accordance with some embodiments can be administered daily, every other day, every other week, every other month, etc., with a single application or multiple applications per day of administration, such as applications 2, 3, 4 or more times per day of administration.

Many Tβ4 isoforms have been identified and have about 70%, or about 75%, or about 80% or more homology to the known amino acid sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET (SEQ ID NO: 3) or LKKTNT (SEQ ID NO: 4), that appears to be involved in mediating actin sequestration or binding. Although not wishing to be bound by any specific theory, the activity of peptide agents as described herein may be due, at least in part, to the anti-inflammatory activity of such agents. Tβ4 also can modulate actin polymerization (e.g. β-thymosins appear to depolymerize F-actin by sequestering free G-actin). Tβ4's ability to modulate actin polymerization may be due to its ability to bind to or sequester actin via the LKKTET (SEQ ID NO: 3) or LKKTNT (SEQ ID NO: 4) sequence. Thus, as with Tβ4, other proteins which are anti-inflammatory and/or bind or sequester actin, or modulate actin polymerization, including Tβ4 isoforms having the amino acid sequence LKKTET (SEQ ID NO: 3) or LKKTNT (SEQ ID NO: 4), are likely to be effective, alone or in a combination with Tβ4, as set forth herein.

Thus, it is specifically contemplated that known LKKTET or LKKTNT peptides as described herein, including Tβ4 isoforms, such as Tβ4$^{ala}$, Tβ9, Tβ10, Tβ11, Tβ12, Tβ13, Tβ14 and Tβ15, as well as Tβ4 isoforms not yet identified, will be useful in the methods of some embodiments. As such LKKTET (SEQ ID NO: 3) or LKKTNT (SEQ ID NO: 4) peptides as described herein, including Tβ4 isoforms, are useful in the methods of some embodiments, including the methods practiced in a subject. Some embodiments provide pharmaceutical compositions comprising LKKTET (SEQ ID NO: 3) or LKKTNT (SEQ ID NO: 4) peptides as described herein, including Tβ4, as well as Tβ4 isoforms Tβ4$^{ala}$, Tβ9, Tβ10, Tβ11, Tβ12, Tβ13, Tβ14 and Tβ15, and a pharmaceutically acceptable carrier.

In addition, other agents or proteins having anti inflammatory activity and/or actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET (SEQ ID NO: 3) or LKKTNT (SEQ ID NO: 4), for example, can similarly be employed in the methods of some embodiments. Such proteins may include gelsolin, vitamin D binding protein (DBP), profilin, cofilin, depactin, Dnasel, vilin, fragmin, severin, capping protein, β-actinin and acumentin, for example. As such methods include those practiced in a subject, some embodiments further provides pharmaceutical compositions comprising gelsolin, vitamin D binding protein (DBP), profilin, cofilin, depactin, Dnasel, vilin, fragmin, severin, capping protein, β-actinin and acumentin as set forth herein. Some embodiments include the use of a polypeptide comprising the amino acid sequence LKKTET (SEQ ID NO: 3) or LKKTNT (SEQ ID NO: 4) and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Tβ4 has been localized to a number of tissue and cell types and thus, agents which stimulate the production of an LKKTET (SEQ ID NO: 3) or LKKTNT (SEQ ID NO: 4) peptide such as Tβ4 or another peptide agent as described herein, can be added to or comprise a composition to effect production of a peptide agent from a tissue and/or a cell. Such stimulating agents may include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α1 (Tα1) and vascular endothelial growth factor (VEGF). More preferably, the stimulating agent is transforming growth factor beta (TGF-β) or other members of the TGF-β superfamily.

In accordance with some embodiments, subjects are treated with a stimulating agent that stimulates production in the subject of a peptide agent as defined herein.

Additionally, other agents that assist in promoting recovery of peripheral neuropathy may be added to a composition along with a peptide agent as described herein. For example, and not by way of limitation, a peptide agent as described herein alone or in combination can be added in combination with any one or more of the following agents: antibiotics, VEGF, KGF, FGF, PDGF, TGFβ, IGF-1, IGF-2, IL-1, prothymosin α and/or thymosin α in a therapeutically effective amount.

Some embodiments comprise a pharmaceutical composition comprising a therapeutically effective amount of a peptide agent as described herein in a pharmaceutically acceptable carrier.

The actual dosage or reagent, formulation or composition that provides treatment may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

Suitable formulations may include a peptide agent as described herein at a concentration within the range of about 0.001-50% by weight, more preferably within the range of about 0.01-0.1% by weight, most preferably about 0.05% by weight.

The therapeutic approaches described herein with respect to some embodiments involve various routes of administration or delivery of a peptide agent as described herein, including any conventional administration techniques (for example, but not limited to, direct administration, local injection, inhalation, or systemic administration), to a subject. The methods and compositions using or containing a peptide agent as described herein may be formulated into pharmaceutical compositions by admixture with pharmaceutically acceptable non-toxic excipients or carriers.

EXAMPLES

The following examples are provided without limiting the invention to only those embodiments described herein and without disclaiming other embodiments or subject matter.

Example 1

Background

Peripheral neuropathy is one of the most common and disabling complications of diabetes mellitus. We evaluated whether thymosin β4 ("Tβ4") ameliorates diabetes—induced neurovascular dysfunction in the sciatic nerve and promotes recovery of neurological function from diabetic peripheral neuropathy. The results of our evaluation show that thymosin beta 4 promotes the recovery of peripheral neuropathy in type II diabetic mice.

Methods and Results:

Tβ4 treatment of db/db mice which had peripheral neuropathy substantially increased functional vascular density and regional blood flow in the sciatic nerve, and improved nerve function. Tβ4 upregulated Angiopoietin-1 (Ang1) expression, but suppressed Ang2 expression in endothelial and Schwann cells in the diabetic sciatic nerve. In vitro, incubation of Human Umbilical Vein Endothelial Cells (HUVECs) with Tβ4 under high glucose condition completely abolished high glucose-downregulated Ang1 expression and high glucose-reduced capillary-like tube formation. Moreover, incubation of HUVECs under high glucose with conditioned medium collected from Human Schwann cells (HSCs) treated with Tβ4 significantly reversed high glucose-decreased capillary-like tube formation. A neutralized antibody against Tie2 suppressed the effect of Tβ4 and the condition medium on HUVECs. Tβ4 activated Akt on HSCs, while blockage of the PI3K/Akt with a PI3K inhibitor, LY294003, inactivated Akt and suppressed the effect of Tβ4 on Ang1 upregulation.

Our results demonstrate that Tβ4 remarkably and unexpectedly improved vascular function in the sciatic nerve and peripheral nerve function in a mouse model of peripheral diabetic neuropathy. Without being bound by any specific theory, Tβ4 may act on endothelial cells and Schwann cells to preserve and/or restore vascular function in the sciatic nerve which facilitates improvement of peripheral nerve function under diabetic neuropathy.

Peripheral neuropathy is one of the most common and disabling complications of diabetes mellitus. Studies of peripheral diabetic neuropathy from experimental animals and humans indicate that the development of diabetic neuropathy is closely associated with marked neurovascular dysfunction[1-3]. Vascular dysfunction precedes the appearance of nerve conduction velocity deficits, leading to nerve damage[3-5].

Thymosin beta 4 (Tβ4), a small 4.9 kDa polypeptide of 43 amino acids, is a major intracellular G-actin-sequestering peptide[9]. Among its multiple biological functions, Tβ4 promotes angiogenesis after myocardial infarction and vasculogenesis during development[10, 11]. Tβ4 is currently under a phase II clinic trial for the treatment of patients with acute myocardial infarction[12]. Whether Tβ4 has therapeutic effect on diabetic neuropathy was not known before our work.

The angiopoietins (Ang1 and Ang2) and their receptor Tie-2 regulate vascular development and homeostasis[17, 18]. Ang-1 promotes vascular stabilization and maturation whereas Ang2 acts as a partial agonist or antagonist of Ang1 signaling, depending on vascular endothelial growth factor (VEGF) bioavailability[17, 19, 20]. The Ang/Tie2 signaling pathway plays an important role in mediating vascular function under diabetes[21, 22]. Hyperglycemia downregulates Ang1 and upregulates Ang2[21, 23]. Increases in Ang1 levels normalize diabetes induced immature vasculature[24]. Ang1 by increasing angiogenesis reduces myocardial infarction, whereas an elevation of Ang2 levels exacerbates the infarction in diabetic rats[21]. Patients with peripheral diabetic neuropathy have elevated levels of circulating Ang2[25]. However, the effect of the Ang/Tie2 signaling pathway on peripheral diabetic neuropathy has not been extensively studied.

Using a mouse model of type II diabetes, we evaluated whether treatment of peripheral diabetic neuropathy with Tβ4 ameliorates neurovascular dysfunction and improves peripheral nerve function. In addition, we evaluated the effect of Tβ4 on the Ang/Tie2 signaling pathway under peripheral diabetic neuropathy.

Methods:

Animals—

All experimental procedures were carried out in accordance with NIH Guide for the Care and Use of Laboratory Animals and approved by the institutional Animal Care and Use Committee of Henry Ford Hospital. Male BKS.Cg-m+/+Lepr$^{db}$/J(db/db) mice (Jackson Laboratories, Bar Harbor, Me.) aged 20 weeks were used. Age-matched heterozygotes mice (db/m), a non-penetrant genotype (Jackson Laboratories), were used as the control animals.

Tβ4 Treatment— db/db mice at age 20 weeks were treated with Tβ4 at a dose of 6 mg/kg or 24 mg/kg (RegeneRx, Inc, intraperitoneal injection, i.p.), every 3 days for 4 weeks (n=10/group). db/db mice (n=10/group) at the same age treated with same volume of saline were used as a control group. Age-matched db/m mice treated with Tβ4 (6 mg/kg i.p. every 3 days, n=10/group) or saline (n=10/group) were used as additional control groups. All mice were sacrificed 8 weeks after the initial treatment. Doses of Tβ4 were selected based on published studies[13].

Measurement of Regional Sciatic Nerve Blood Flow by Laser Doppler Flowmetry—

Regional sciatic nerve blood flow was measured at the end of the experiments (8 weeks after the initial treatment) using laser Doppler flowmetry (LDF PeriFlux PF4, Perimed AB, Järfälla, Sweden)[26]. Briefly, under anesthesia the mouse was mounted on a stereotactic frame under anesthetization. The left sciatic nerve was exposed in the mid-thigh region and animal rectal temperature was kept at 37±1.0° C. during the measurement period using a feedback controlled water bath. Using a micromanipulator, a LDF probe was placed at the surface of the sciatic nerve and relative flow values expressed as perfusion units were recorded every 5 min for a total of 3 time. Regional sciatic nerve blood flow values from db/m mice were used as base line values and data are presented as a percentage of baseline values.

Neurophysiological Measurements—

Sciatic nerve conduction velocity was assessed with orthodromic recording techniques, as described before[27]. Briefly, trigger single square wave current pulses were delivered using an isolated pulse stimulator (Model 2100, A-M Systems, Everett, Wash.). The simultaneous electromyographies were recorded by two sterilized electrodes placed into the intrinsic foot muscles with a Grass Amplifier (Model P5, Grass Instruments, Quincy, Mass.). During the measurements, animal rectal temperature was kept at 37±1.0° C. using a feedback controlled water bath. Motor nerve conduction velocity (MCV) and sensory nerve conduction velocity (SCV) were calculated according to a published study[7].

Tail-Flick and Hot Plate Tests—

To examine thermal hyperalgesia, tail-flick and hot plate tests were employed according to published methods[27-29]. Briefly, for tail-flick test, a mouse was restrained in a conical polypropylene tube with an opening through which its tail was exposed. Approximately 2 cm of the mouse's tail was immersed into a 52° C.±0.2 water bath and the time until the rodent flicks or removes its tail was recorded[28]. For hot plate test, a mouse was placed within a plexiglass chamber on a transparent glass surface and allowed to acclimate for at least 20 min. A thermal stimulation meter (IITC Model 39 Hot Plate Analgesia Meter, IITC Life Science, CA) was used with floor temperature at 55° C. (manufacturer's setup). The latency of paw withdrawal in response to the radiant heat was recorded[29]. Cut-off periods of 10 and 15 s were employed to avoid tissue damage for the tail-flick and hot plate tests, respectively. In both tests, at least three readings per animal were taken at 15 min intervals, and the average was calculated.

Immunohistochemistry—

The left and right side sciatic nerves were isolated at the mid-thigh level, fixed in 4% paraformaldehyde, and embedded in paraffin according to published protocol[27]. Three cross sections (6-μm-thick) or three longitudinal sections (6-μm-thick) in the one in ten series (60 μm apart) for each animal were used for immunostaining according to our published protocols[27]. The following primary antibodies were used: polyclonal rabbit anti-Ang1 (1:2000; Abcam, Cambridge, Mass.), monoclonal mouse anti-CD31 antibody (1:500, BD Biosciences, San Jose, Calif.), polyclonal rabbit Anti-Von Willebrand Factor (vWF) (1:300, Dako, Carpenteria, Calif.), monoclonal mouse anti-occludin (1:200, Zymed, San Francisco, Calif.) and polyclonal rabbit anti-S100 (1:400, Abcam). Rabbit or goat IgG was used as a negative control. Sections were counterstained with 4',6-Diamidino-2-phenylindole (DAPI) (1:5000).

Image Analysis and Quantification—

To examine microvascular perfusion in the sciatic nerve, fluorescein isothiocyanate (FITC)-dextran ($2 \times 10^6$ molecular weight, Sigma; 0.2 mL of 50 mg/mL) was administered intravenously to the mice 10 min before sacrifice[30]. The sciatic nerves were rapidly removed and placed in 2% of paraformaldehyde for 2 hours. And then, nerves were embedded in OCT compound for frozen cross sections. Three cross frozen sections (20 μm/section, thickness) at 60 μm intervals from each mouse were used for image analysis. The sections were digitized under a 20× microscope objective (Zeiss Axiophot) via a Micro Computer Imaging Device (MCID) system (Imaging Research Inc, St. Catharines, ON, Canada)[30]. The total number of FITC-dextran perfused vessels was counted and divided by the total tissue-area to determine vascular density.

For analysis of vWF immunoreactive vascular morphology and density, three sections spaced at 60 μm intervals from each mouse were used. Three fields of the view per section were randomly imaged under a 20× objective and vWF immunoreactive vascular perimeter and total number of vWF positive vessels were measured using MCID.

All analysis was conducted with the examiner blinded to the identity of the samples being studied.

Cell Culture—

We defined a normal glucose medium (NG) as a medium containing 5 mM glucose, while a high glucose medium (HG) is referred to a medium containing 30 mM glucose, which was chosen to match glucose levels prevalent in uncontrolled diabetic patients[31]. These glucose concentrations for the in vitro hyperglycemia experiments have been used by others[32, 33].

Human Schwann cells (HSCs, ScienCell Research Laboratories, Carlsbad, Calif.) derived from primary culture and Human Umbilical Vein Endothelial Cells (HUVEC, American Type Culture Collection, ATCC, Manassas, Va.) were cultured according to the manufacturer's instructions (ScienCell Research Laboratories and ATCC). To examine the effect of Tβ4 on HSCs, HSCs were cultured under the NG or HG condition in the presence of different concentrations of Tβ4 (0, 25, 50 and 100 ng/ml) for 24 or 72 hours. The cells were harvested for real-time RT-PCR and Western blot analysis. To collect conditioned medium from HSCs, $2.5 \times 10^6$ HSCs were plated onto a 35-mm-diameter dish in 1.2 ml of defined medium. The cells were cultured under the NG or HG conditions in the presence or absence of Tβ4 (100 ng/ml) for 24 h. HSCs were then washed three times with PBS and a fresh serum free medium was added to avoid excessive Tβ4 contamination, The cells were cultured for additional 48 h, the supernatant (conditioned medium) was collected, centrifuged for 10 min at 1000 rpm, and stored at −80° C.

To assess the effect of Tβ4 on in vitro angiogenesis, a capillary-like tube assay was used[34-36]. Briefly, HUVECs ($2 \times 10^4$ cells) were cultured on 96-well plate coated by MATRIGEL® (BD Biosciences, Rockville, Md.) in the conditioned medium or Dulbecco's Modified Eagle Medium (DMEM) in the presence or absence of Tβ4 (0, 25, 50 and 100 ng/ml) for 5 h. Total length of tubes was measured in 3 random fields from each well using MCID[37].

Real-Time RT-PCR—

Total RNA samples from cells were isolated using the Stratagene Absolutely RNA MicroRNA isolation kit (Stratagene, La Jolla, Calif.), according to the manufacturer's instructions. The complementary DNA (cDNA) was reversely transcribed from the same concentrations of total RNA products using random hexamers and M-MLV reverse-transcriptase (Invitrogen, Carlsbad, Calif.). Using the SYBR Green real-time PCR method[38], quantitative PCR was performed on an ABI 7000 PCR instrument (Applied Biosystems, Foster City, Calif.) by means of three-stage program parameters provided by the manufacturer, as follows; 2 min at 50° C., 10 min at 95° C., and then 40 cycles of 15 s at 95° C. and 1 min at 60° C. Specificity of the produced amplification product was confirmed by examination of dissociation reaction plots. Each sample was tested in triplicate, and samples obtained from three independent experiments were used for analysis of relative gene expression using the $2^{\Delta\Delta CT}$ method[39]. The following primers for real-time PCR were designed using Primer Express software (ABI): Glyceraldehyde-3-phosphate dehydrogenase (GAPDH) (FWD, AGA ACA TCA TCC CTG CAT CC (SEQ ID NO: 7); REV, CAC ATT GGG GGT AGG AAC AC (SEQ ID NO: 8)) and Ang1 (FWD, GAA GGG AAC CGA GCC TAT TC (SEQ ID NO: 9); REV, GCT GAA ATC AGC ACC GTG TA (SEQ ID NO: 10)), Ang2 (FWD, CAG ATC CGG GCT CTA GAC AG (SEQ ID NO: 11); REV, TCC GGA AAT CGT TCT TCA TC (SEQ ID NO: 12)).

Western Blot Analysis—

Western blot was performed according to published methods[38]. Briefly, equal amounts of proteins were loaded on 10% SDS-polyacrylamide gel. After electrophoresis, the proteins were transferred to nitrocellulose membranes, and the blots were subsequently probed with the following antibodies: polyclonal rabbit anti-Ang1 (1:1000; Abcam, Cambridge, Mass.), polyclonal rabbit anti-Ang2 (1:1000; Abcam), Phospho-Akt (1:1000, Cell Signaling Technology, Inc. Danvers, Mass.) and Akt (1:1000, Cell Signaling Technology). For detection, horseradish peroxidase-conjugated secondary antibodies were used (1:2000) followed by enhanced chemiluminescence development (Pierce, Rockford, Ill.). Normalization of results was ensured by running parallel Western blot with β-actin antibody. The optical density was quantified using an image processing and analysis program (Scion Image, Ederick, Mass.).

Statistical Analysis—

Data were evaluated for normality. Data transformation was considered if data were not normal. As a result, ranked data were used for the analysis. The global test using Generalize Estimating Equation (GEE) was implemented to test the group difference on functional recovery measured. The analysis started testing the treatment overall group effect, followed by a subgroup analysis at the 0.05 level, if the overall group effect was detected at the 0.05 level. The global test on multiple outcomes is more efficient than a single outcome, when the dose effects are consistent on all the outcomes (e.g., the positive correlation). A significant dose effect on the functional recovery (p<0.05 based on the global test) would be further tested on individual outcome at 0.05. One-way ANOVA was used to test the overall group effect. The data are presented as mean±SE. A value of P<0.05 was taken as significant.

Results:

Our data indicated that Tβ4 improves diabetes-induced vascular dysfunction in the sciatic nerve.

Figure 2:
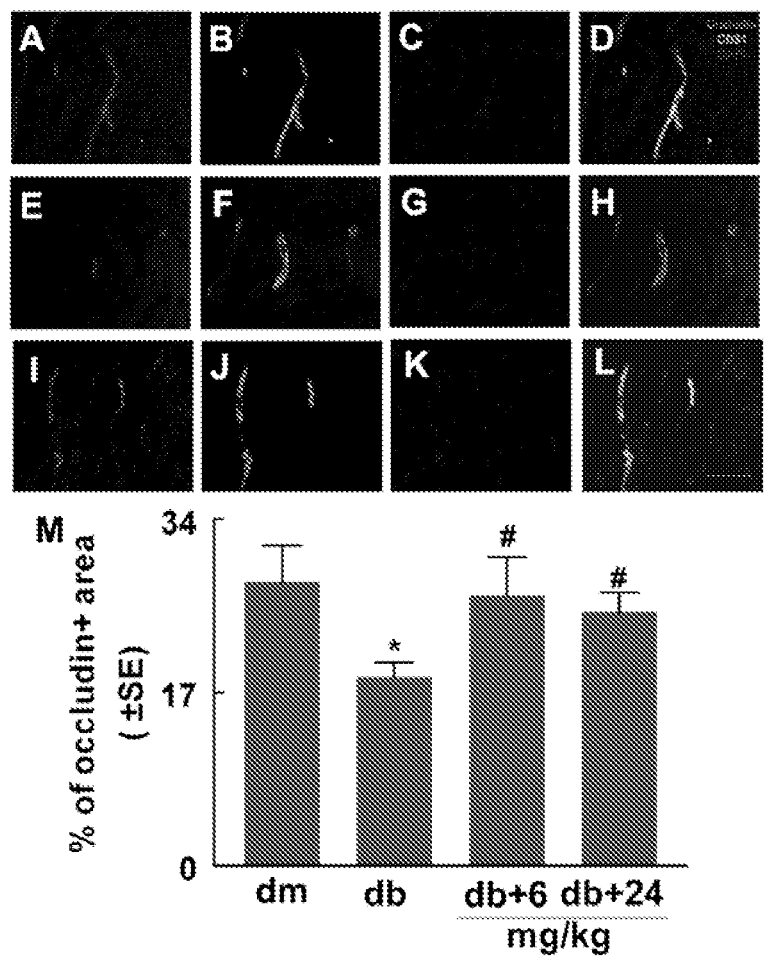
FIG. 2 is images and data representations showing data that indicates that Tβ4 increases occludin immunoreactive area in the vessel walls.

To examine whether db/db mice develop impairment of neurovasculature, we examined microvessels of the vasa nervora in the sciatic nerve of the mice at age of 28 weeks. Analysis of vWF immunoreactive vessels of the vasa nervorum revealed that blood vessel perimeter in the db/db mice was significantly reduced compared to that in the age-matched db/m mice, although vascular density was not significant different between these two groups (73.5±10.5 vs. 56.9±6.4 in db/m mice, p>0.05) (FIG. 1). FIG. 1 contains data showing that Tβ4 improves vascular function in the sciatic nerve. Panels A to C show vWF immunoreactive blood vessels at the cross section of the sciatic nerve from a representative db/m mouse (A), db/db mouse treated with saline (B), and db/db mouse treated with Tβ4 (24 mg/kg, C). Panels D to F show FITC-dextran perfused vessels at cross section of the sciatic nerve from a representative db/m mouse (D), db/db mouse treated with saline (E), and db/db mouse treated with Tβ4 (24 mg/kg, F). Panels G and I show quantitative data of vWF immunoreactive vascular perimeters (G, n=6/group), and density of FITC-dextran perfused vessels (H, n=4/group), occludin immunoreactive vessels (I, n=6/group) and percentage changes of sciatic nerve blood flow with a reference of db/m mice at 100% (J, n=4/group). dm=db/m mouse; db=db/db mouse. In addition, the db/db mice exhibited substantial reduction of occludin, a tight junction protein, immunoreactive vessels (FIG. 1). To examine whether the reduced perimeter in the db/db mice affects vascular function, we measured plasma-perfused microvessels, which represents functional vessels[7, 26] and regional blood flow. To measure plasma-perfused vessels, we intravenously injected FITC-dextran into the mice and then sacrifice them 10 minutes after injection, which provides enough time for the FITC-dextran to circulate throughout the entire vascular system under physiological conditions. Quantitative analysis of FITC-dextran perfused vessels on cross sections of the sciatic nerves revealed that the db/db mice had a significant reduction in microvascular densities perfused by FITC-dextran compared to the db/m mice (FIG. 1). In parallel, sciatic nerve blood flow measured by LDF was significantly reduced in the db/db mice compared to that in the db/m mice (FIG. 1). Together, these data indicate that diabetes induces vascular dysfunction in the sciatic nerve, which is consistent with published studies 6, 7, 40. However, the db/db mice treated with Tβ4 at doses of 6 and 24 mg/kg for 4 weeks starting at animal age of 20 weeks exhibited significant increases in vascular perimeter, occludin immunoreactive vessels, the density of FITC-dextran perfused vessels and sciatic nerve blood flow at age of 28 weeks compared to the db/db mice treated with saline, which were close to levels measured in the db/m mice (FIG. 1). Similarly, the data of FIG. 2 show that Tβ4 increases occludin immunoreactive area in the vessel walls. Panels A to L show that CD31 immunoreactive vessels (green) were occludin positive (red) from a representative db/m mouse (A-D, dm), db/db mouse treated with saline (E-H, db), and db/db mouse treated with Tβ4 (24 mg/kg, I-L). Panel M shows quantitative data of the percentage of occludin immunoreactive area. #p<0.05 vs db/db mice treated with saline. n=6/group. These data indicate that Tβ4 ameliorates diabetes-induced vascular dysfunction in the sciatic nerve.

Our data indicated that Tβ4 improves neurological function in the diabetic mouse.

Figure 3:
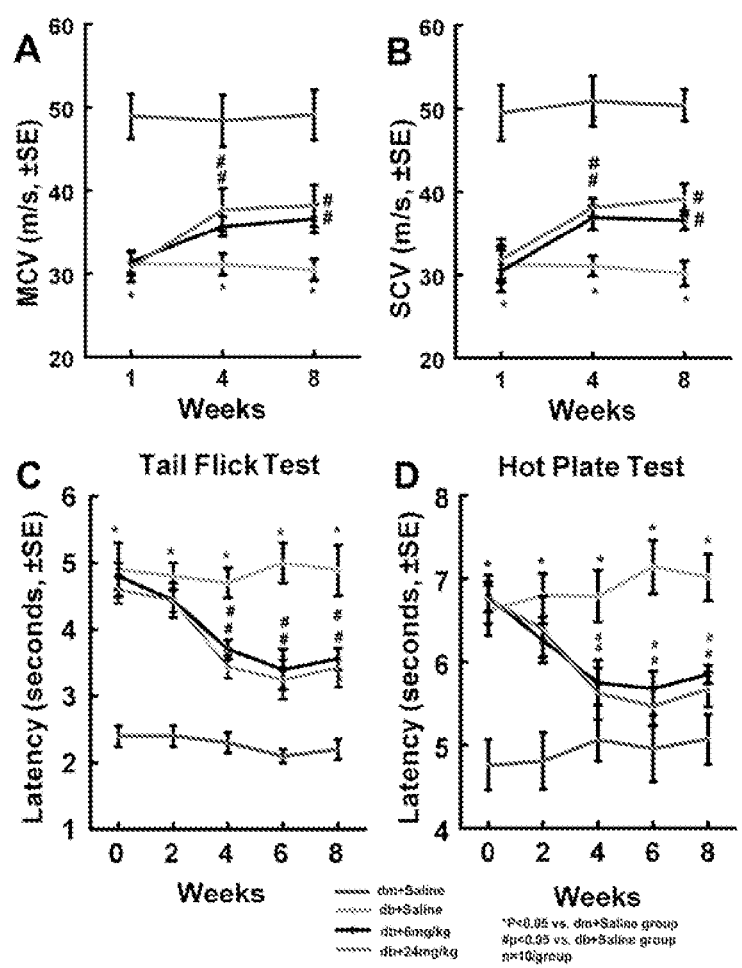
FIGS. 3 and 4 are data representations showing data that indicates the effect of Tβ4 on neurological function.
Figure 4:
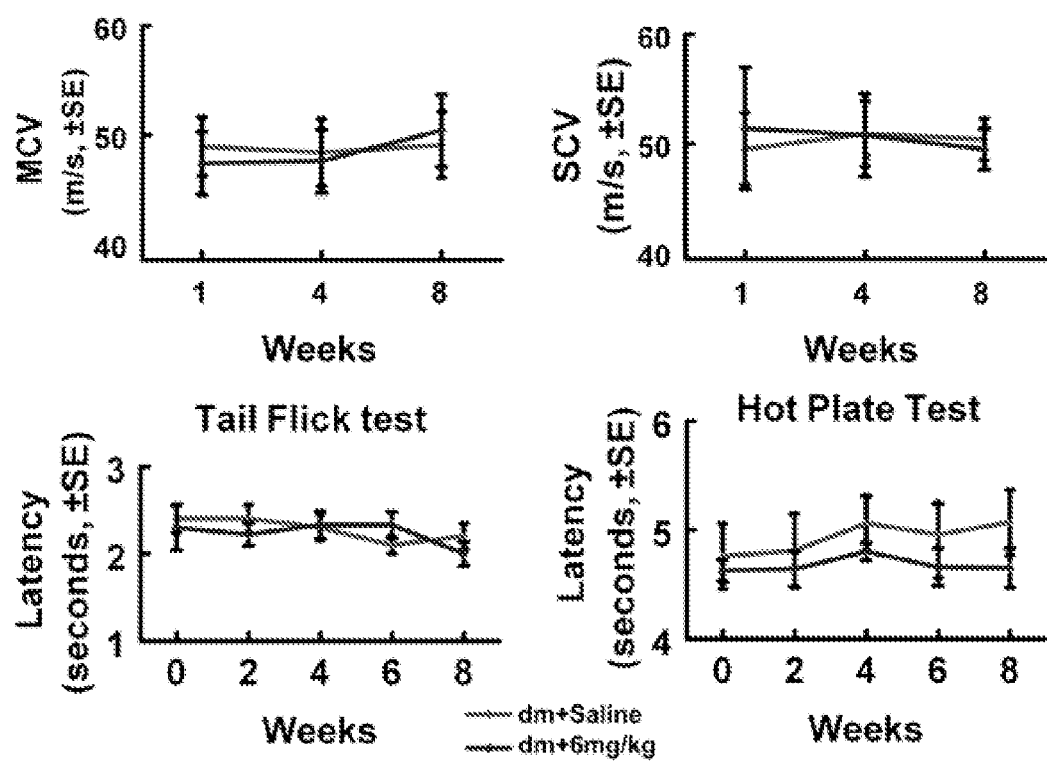

Impairment of peripheral nerve conduction is a key indicator for diabetic patients having peripheral neuropathy[41, 42] and vascular dysfunction affects nerve conduction[4, 5]. We therefore evaluated whether augmentation of regional blood flow by Tβ4 affects motor and sensory conducting velocity (MCV and SCV) in the sciatic nerve. Electrophysiological recordings showed that MCV and SCV were significantly slowed in db/db mice compared to those of the age matched db/m mice (FIG. 3), which are comparable to values reported by others[7, 43]. FIG. 3 shows data relating to the effect of Tβ4 on neurological function. Treatment of db/db mice with Tβ4 improves neurological function measured by MCV (A), SCV (B), Tail flick test (C) and Hot plate test (D). *P<0.05 and #P<0.05 versus the db/m mouse and the db/db mouse treated with saline, respectively. n=10/group. dm=db/m mouse; db=db/db mouse. Treatment of the db/db mice with Tβ4 at doses of 6 and 24 mg/kg for 4 weeks showed marked improvement in both MCV and SCV at the end of Tβ4 treatment and at 4 weeks after termination of the treatment compared with saline-treated db/db mice (FIG. 3). We then examined the effect of Tβ4 treatment on sensory function by measuring the thermal latency with tail flick and hot plate tests. Treatment of the db/db mice with Tβ4 markedly improved the thermal latency starting at the end of Tβ4 treatment, which persisted for at least 4 weeks after termination of the treatment (the end of experimental period) (FIG. 4). To examine the effect of Tβ4 on non-diabetic mice, we treated db/m mice with Tβ4 at a dose of 6 mg/kg and did not detect any functional changes as measured by the methods listed above. See FIG. 4. Treatment of db/m mice with Tβ4 at 6 mg/kg did not change neurological function measured by MCV (A), SCV (B), Tail flick test (C) and Hot plate test (D). n=10 mice/group. dm=db/m mouse. These data indicate that Tβ4 improves peripheral nerve function in the diabetic mouse.

Treatment of the db/db mouse with Tβ4 did not significantly alter blood glucose levels and animal body weight (Table 1 and 2).

Our data indicated that Tβ4 regulates pro-angiogenic genes in the sciatic nerve.

Figure 5:
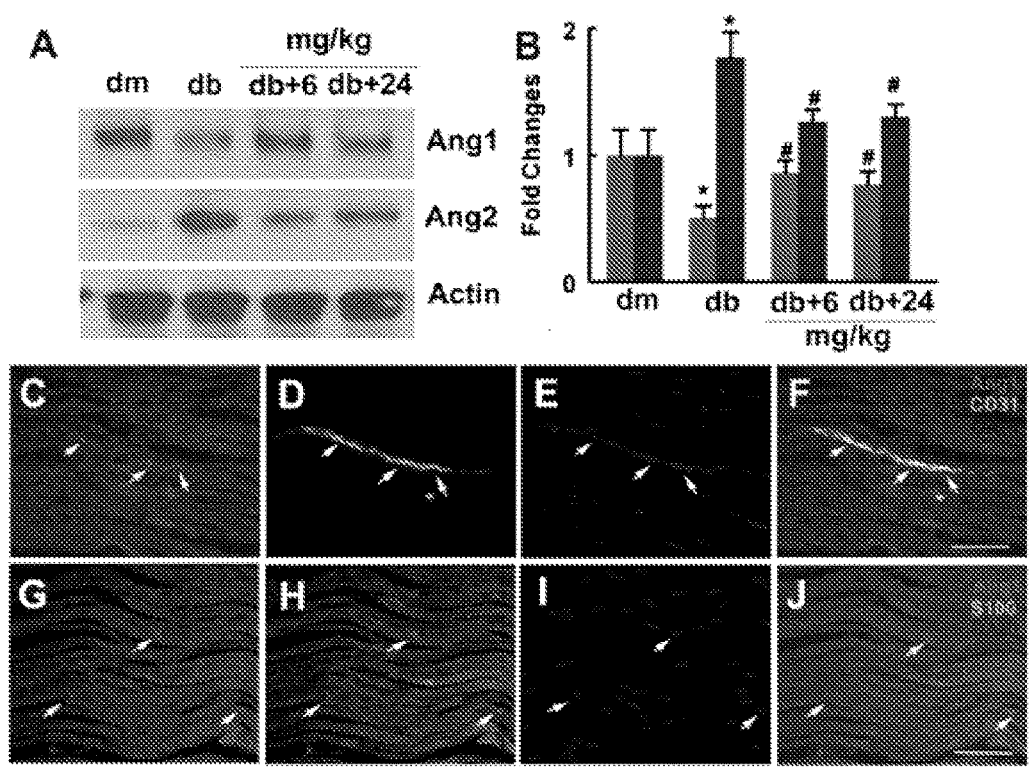
FIG. 5 is images and data representations showing data that indicates that Tβ4 upregulates Ang 1 expression on endothelial cells and Schwann cells in a diabetic mouse model.

Alterations of Ang1 and Ang2 levels have been detected in diabetic patients and experimental diabetes[21, 25]. To examine the effect of Tβ4 on these angiogenic genes, we measured protein levels of Ang1 and Ang2. FIG. 5 shows data indicating that Tβ4 upregulates Ang 1 expression on endothelial cells and Schwann cells in the diabetic mouse. Western blot analysis (A and B) of Ang1 and Ang2 levels in sciatic nerve tissue and β-actin was used as an internal control. Representative images of double immunofluorescent staining show that Ang1 immunoreactivity (C, F, G, J, red, arrows) was colocalized to CD31 positive vessels (D, F, green) and S100 positive Schwann cells (H, J, green, arrows). *P<0.05 and #P<0.05 versus the db/m mouse and the saline treated db/db mouse, respectively. n=6/group. dm=db/m mouse; db=db/db mouse. Western blot analysis of the sciatic nerve showed substantial reduction of Ang1 levels and an increase in Ang2 levels in the db/db mouse (FIG. 5), whereas treatment of the db/db mouse with Tβ4 significantly increased Ang1 expression, but decreased Ang2 expression (FIG. 5). Double immunostaining revealed that Ang1 immunoreactive cells were CD31 (a marker of endothelial cells) and S100 (a marker of Schwann cells) positive (FIG. 5). Collectively, these data indicate that Tβ4 upregulates Ang1 expression on endothelial cells and Schwann cells in the diabetic mouse.

Our data indicated that the Ang/Tie2 signaling pathway mediates the effect of Tβ4 on endothelial function.

Figure 6:
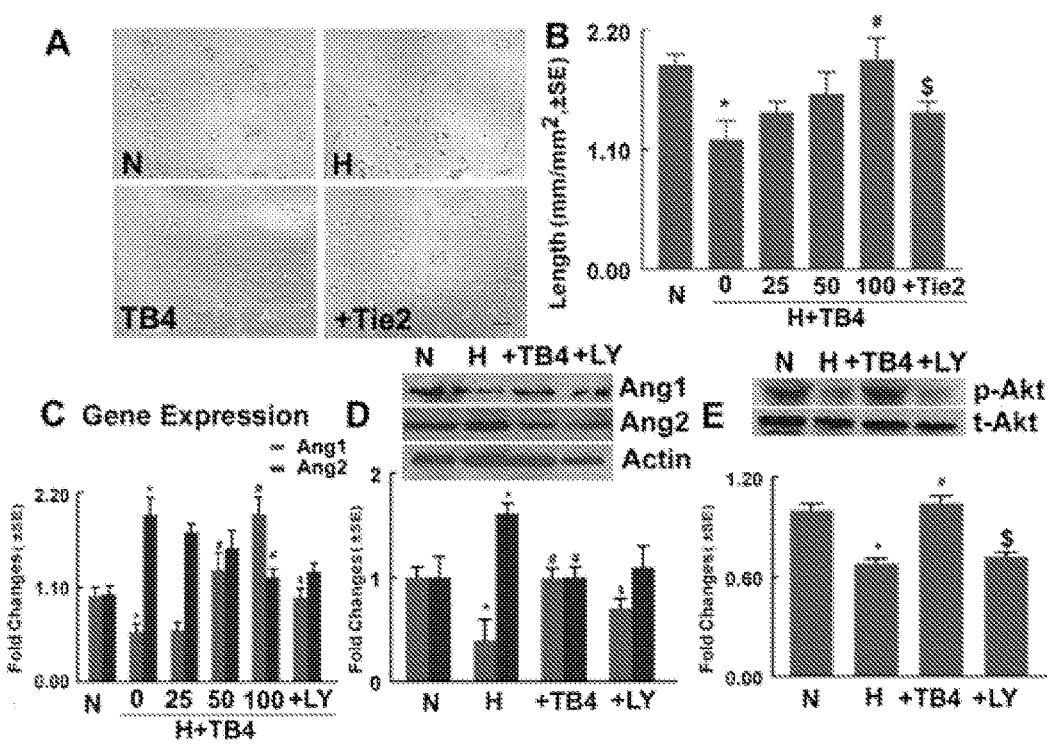
FIG. 6 is images and data representation showing data that indicates that the Ang/Tie2 signaling pathway mediates the effect of Tβ4 on endothelial function.

Aforementioned in vivo data suggest that Ang1 and Ang2 genes mediate Tβ4-improved vascular function in the diabetic mouse. To examine a cause-effect of these genes on endothelial cells under hyperglycemia condition, we performed in vitro experiments using a capillary-like tube formation assay, which is widely used to examine in vitro endothelial function[34, 35, 37, 44]. FIG. 6 shows data indicating that the Ang/Tie2 signaling pathway mediates the effect of Tβ4 on endothelial function. Representative microscopic images (A) and quantitative data (B) show capillary-like tube formation in HUVECs cultured in normal glucose (N), high glucose (H), high glucose with Tβ4 (H+TB4, 100 ng/ml), and high glucose with Tβ4 in the presence of a neutralizing antibody against Tie2 (+Tie2, 5 μg/ml). Real-time RT-PCR (C) and Western blot (D) data show mRNA and protein levels of Ang1 and Ang2 in HUVECs cultured with normal glucose (N), high glucose (H), high glucose with Tβ4 (+TB4), and high glucose with Tβ4 in the presence of LY294003 (+LY, 10 pM). Panel E shows Western blot analysis of pAkt and total Akt in HUVECs cultured under different conditions listed above. GAPDH and β-actin were used as internal controls for mRNA and proteins, respectively. *P<0.05, #P<0.05 and $P<0.05 versus the normal glucose (N), high glucose (H) and high glucose with Tβ4 (100 ng/ml) groups, respectively. n=6/group. Incubation of HUVECs under high glucose conditions decreased in capillary-like tube formation compared to HUVECs cultured under normal glucose conditions (FIG. 6). However, Tβ4 suppressed the effect of high glucose on reduction of capillary-like tube formation (FIG. 6). Quantitative RT-PCR and Western blot analysis showed that incubation of HUVECs with high glucose substantially decreased and increased Ang1 and Ang2 expression, respectively (FIG. 6), whereas Tβ4 abolished high glucose-induced expression of Ang1 and Ang2 (FIG. 6). Blockage of Tie2, a receptor of Ang1 and Ang2, with a naturalization antibody against Tie2 inhibited Tβ4-increased capillary-like tube formation (FIG. 6). These data indicate that the Ang/Tie2 signaling pathway plays an important role in mediating Tβ4-improved endothelial function under hyperglycemia.

Our data indicated that Ang1 secreted by Tβ4-treated Schwann cells improves endothelial function.

Figure 7:
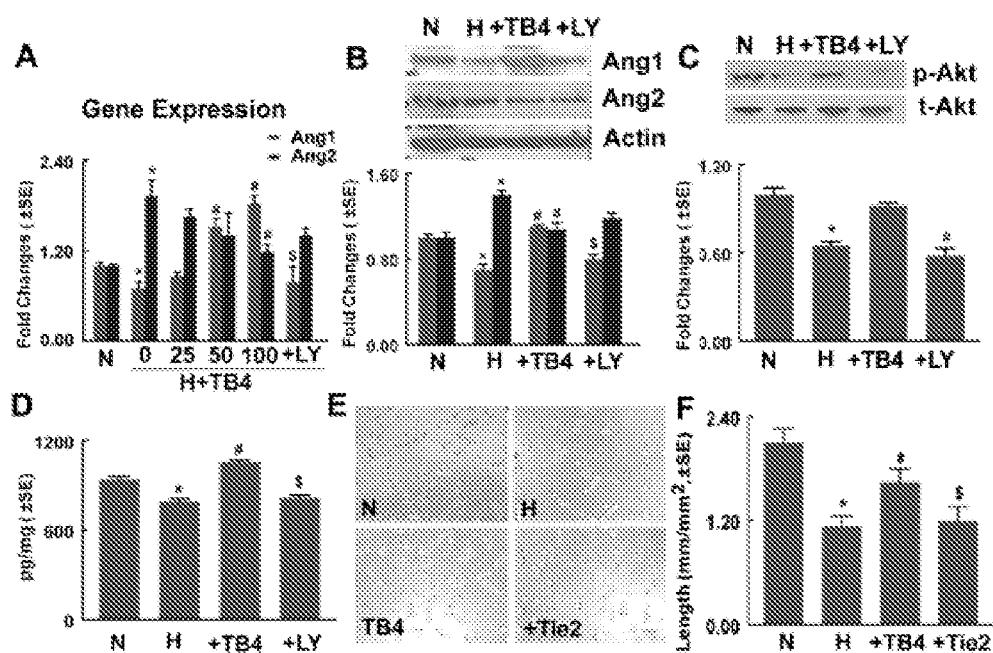
FIG. 7 is images and data representation showing data that indicates that indicating that Ang1 secreted by Tβ4-treated Schwann cells improves endothelial function.

In addition to endothelial cells, our in vivo double immunostaining data showed that Schwann cells expressed Ang1. We therefore, examined the effect of Tβ4 on expression of angiopoietin expression in Schwann cells. FIG. 7 shows data indicating that Ang1 secreted by Tβ4-treated Schwann cells improves endothelial function. Real-time RT-PCR (A) and Western blot (B) data show mRNA and protein levels of Ang1 and Ang2 in HSCs cultured with normal glucose (N), high glucose (H), high glucose with Tβ4 (+TB4), and high glucose with Tβ4 in the presence of LY294003 (+LY). Panel C shows Western blot analysis of pAkt and total Akt in HSCs cultured under different conditions listed above. GAPDH and β-actin were used as internal controls for mRNA and proteins, respectively. Panel D shows ELISA data of Ang1 levels in supernatants harvested from HSCs cultured with normal glucose (N), high glucose (H), high glucose and Tβ4 (+TB4, 100 ng/ml), and high glucose and Tβ4 in the presence of LY294003 (+LY). Representative microscopic images (E) and quantitative data (F) show capillary-like tube formation in HUVECs cultured with the conditioned medium collected from HSCs in normal glucose (N), high glucose (H), high glucose and Tβ4 (+TB4, 100 ng/ml), and high glucose and Tβ4 in the presence of the antibody against Tie2 (+Tie2). *P<0.05, #P<0.05 and $P<0.05 versus the normal glucose (N), high glucose (H) and high glucose with Tβ4 (100 ng/ml) groups, respectively. n=6/group. High glucose substantially downregulated Ang1 and upregulated Ang2, while Tβ4 at a dose of 100 ng/ml suppressed the high glucose effect on the angiopoietin expression in HSCs (FIG. 7, suggesting that Tβ4 also regulates angiopoietin expression in Schwann cells. We then investigated whether Schwann cells secrete Tβ4-upregulated Ang1 that consequently improves vascular function under high glucose condition. Using an ELISA specific to detect mouse Ang1, we measured Ang1 levels in supernatants harvested from HSCs cultured for 48 h. ELISA showed that supernatants from HSCs cultured with high glucose had a significant reduction of Ang1 levels compared to levels in supernatants collected from normal glucose condition, while Tβ4 reversed the effect of the high glucose on Ang1 levels (FIG. 7).

Next, we examined the effect of the supernatants on capillary-like tube formation by culturing HUVECs with conditioned medium harvested from HSCs. Compared to the conditioned medium collected from HSCs cultured with normal glucose, the conditioned medium from HSCs cultured under high glucose condition resulted in a significant decrease of capillary-like tube formation (FIG. 7). In contrast, the conditioned medium collected from HSCs treated with Tβ4 under high glucose condition significantly increased capillary-like tube formation. In the presence of the neutralizing antibody against Tie2, the effect of Tβ4 conditioned medium on capillary-like tube formation was inhibited (FIG. 7). Together, these data indicate that in addition to endothelial Ang1, soluble Ang1 secreted by Tβ4-treated Schwann cells improves endothelial cell function.

Our data indicated that the PI3K/Akt signaling pathway mediates the effect of Tβ4 on Ang 1 expression.

To further evaluate whether intracellular signaling pathways are involved in Tβ4-upregulated Ang1/Ang2 on endothelial cells and Schwann cells, we examined the PI3K/Akt signaling pathway that has been indicated to mediate the effect of Tβ4 on endothelial progenitor cell migration[45]. Western blot analysis of HUVECs and HSCs showed that the high glucose condition markedly decreased pAkt levels compared to the normal glucose (FIGS. 6 and 7). Treatment of HUVECs and HSCs with Tβ4 under the high glucose condition significantly increased pAkt levels, which was fully blocked by a PI3K inhibitor LY294002 (FIGS. 6 and 7), indicating that Tβ4 activates the PI3K/Akt signaling pathway. Moreover, LY294002 completely suppressed the effect of Tβ4 on Ang1, but not Ang2 expression on HUVECs and HSCs under high glucose condition (FIGS. 6 and 7). These data suggest that the PI3K/Akt signaling pathway is involved in Tβ4-regulated Ang1 expression on endothelial and Schwann cells.

Our work for the first time demonstrates that Tβ4 remarkably and unexpectedly improved sciatic nerve vascular function and peripheral nerve function in a mouse model of peripheral diabetic neuropathy. Without being bound by any specific theory, the Ang/Tie2 signaling pathway may mediate the effect of Tβ4 on improved vascular function. The effect of Tβ4 on peripheral diabetic neuropathy has not been investigated previously. Using a well established mouse model of type II diabetes, our work indicates that Tβ4 ameliorates peripheral diabetic neuropathy, evidenced by reduction of sciatic nerve conduction velocity deficits, a key parameter for peripheral diabetic neuropathy, and improvement of responses to thermal and mechanical stimuli. Our data indicate that in some embodiments, without limitation, Tβ4 may be used for the treatment of peripheral diabetic neuropathy.

Studies of peripheral diabetic neuropathy from experimental animals and humans indicate that the development of diabetic neuropathy is closely associated with marked neurovascular dysfunction[1-3]. Vascular dysfunction precedes appearance of nerve conduction velocity deficits, leading to nerve damage[3-5]. Our data demonstrated that Tβ4 substantially increased plasma-perfused vessels and regional blood flow in the sciatic nerve, concomitantly with improvement of neurological function of diabetic neuropathy, suggesting that normalization of vascular function by Tβ4 may contribute to observed reduction of nerve conduction velocity deficits.

The Ang/Tie2 signaling pathway regulates vascular homeostasis[17,18]. Ang1 promotes vascular maturation, while Ang2 acts as a competitive inhibitor of Ang1 for Tie2 binding and destabilizes blood vessels[17,19,28]. Hyperglycemia downregulates Ang1 and upregulates Ang2[21]. Increases in Ang1 levels normalize diabetes induced immature vasculature[24]. Ang1 by increasing angiogenesis reduces myocardial infarction, whereas an elevation of Ang2 levels exacerbates the infarction in diabetic rats[21]. Patients with peripheral diabetic neuropathy have significantly elevated levels of circulating Ang2[25]. Our data show that hyperglycemia downregulated Ang1 and upregulated Ang2 on endothelial cells and Schwann cells, whereas Tβ4 reversed expression of Ang1 and Ang2. Tβ4 is a potent angiogenic factor and regulates angiogenesis and vasculogenesis during development by promoting progenitor cell differentiation and by directing endothelial cell migration[10,46,47].

Our data that blockage of Tie2 with a neutralizing antibody suppressed the effect of Tβ4 on in vitro angiogenesis implicates the Ang/Tie2 signaling pathway in mediating Tβ4-improved vascular function observed in vivo. Without being bound to any specific theory, our data further suggest that Tβ4 regulates Ang1 through the activation of the PI3K/Akt pathway.

Schwann cells secrete numerous factors that regulate degeneration and regeneration peripheral nerves[48-50]. Our work showed that Ang1 and Ang2 secreted by Schwann cells affected endothelial function under hyperglycemia condition, while TN-elevated Ang1 levels on Schwann cells lead to enhancement of in vitro angiogenesis. Thus, without being bound by any specific theory, Tβ4 may act on endothelial cells and Schwann cells to preserve and/or restore vascular function in the sciatic nerve, which facilitates improvement of peripheral nerve function under diabetic neuropathy.

Without limitation to only those embodiments disclosed herein and without disclaimer of other embodiments or subject matter, compositions comprising some embodiments are administered and dosed in accordance with good medical practice, taking into account the clinical condition of the individual patient, the site and method of administration, scheduling of administration, patient age, sex, body weight and other factors known to medical practitioners. The "therapeutically effective amount" for purposes herein is thus determined by such considerations as are known in the art. The amount must be effective to achieve improvement, including but not limited to, decreased indicators of disease, decreased frequency or severity of disease, or improvement or elimination of symptoms and other indicators as are selected as appropriate measures by those skilled in the art.

Administration can be in various ways. It can be administered alone or as an active ingredient in combination with pharmaceutically acceptable carriers, diluents, adjuvants and vehicles. Administration can be oral, subcutaneous or parenteral including intravenous, intraarterial, intramuscular, intraperitoneal, and intranasal administration as well as intrathecal and infusion techniques, or by local administration or direct inoculation to the site of disease or pathological condition. Implants of the compounds are also useful. The patient being treated may be a warm-blooded animal and, in particular, mammals including humans. The pharmaceutically acceptable carriers, diluents, adjuvants and vehicles as well as implant carriers generally refer to inert, non-toxic solid or liquid fillers, diluents or encapsulating material not reacting with the active ingredients of some embodiments.

It is noted that humans are treated generally longer than the experimental animals exemplified herein which treatment has a length proportional to the length of the disease process and drug effectiveness. The doses may be single doses or multiple doses over periods of time. The treatment generally has a length proportional to the length of the disease process and drug effectiveness and the patient species being treated.

When administering some embodiments parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

When necessary, proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for selected embodiments. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. Any vehicle, diluent, or additive used should be compatible with the selected embodiment.

Sterile injectable solutions can be prepared by incorporating the desired embodiment in the required amount of the appropriate solvent with various of the other ingredients, as desired.

A pharmacological formulation comprising some embodiments can be administered to the patient in an injectable formulation containing any compatible carrier, such as various vehicle, adjuvants, additives, and diluents; or the embodiments can be administered parenterally to the patient in the form of slow-release subcutaneous implants or targeted delivery systems. Many other such implants, delivery systems, and modules are well known to those skilled in the art.

Compositions comprising some embodiments may be in any suitable form and for internal or external use. Preparations for internal use include powders, tablets, dispersible granules capsules, solutions, suspensions, and emulsions suitable for oral ingestion or injection.

Topical compositions may also be administered in the form of wound dressings, transdermal patches and the like.

In some embodiments, without limitation to only those disclosed herein and without disclaimer of other embodiments or subject matter, therapeutically effective dosing may be determined in accordance with the subject's condition, level of symptomatology encountered, route and/or frequency of administration, and other considerations and techniques known or available to the skilled artisan and applied consistent with good scientific or medical standards and practice.

Without limitation, some embodiments may be used in conjunction with any type of animal, including but not limited to, humans and other mammals.

All attachments, tables, and cited references are hereby incorporated by reference in their entireties as though fully set forth herein.

It will be appreciated that various changes or modifications may be made to embodiments as described and claimed herein without departing from the spirit and scope thereof. While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements.

The foregoing embodiments are illustrative and not restrictive, and no single feature or element is essential to all possible combinations that may be claimed in this or a later application. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. Where the claims recite "a" or "a first" element of the equivalent thereof, such claims should be understood to include incorporation of one or more such elements, neither requiring nor excluding two or more such elements.

REFERENCES

1. Cameron N E, Eaton S E, Cotter M A, Tesfaye S. Vascular factors and metabolic interactions in the pathogenesis of diabetic neuropathy. Diabetologia. 2001; 44:1973-1988
2. Tesfaye S, Harris N, Jakubowski J J, Mody C, Wilson R M, Rennie I G, et al. Impaired blood flow and arteriovenous shunting in human diabetic neuropathy: A novel technique of nerve photography and fluorescein angiography. Diabetologia. 1993; 36:1266-1274
3. Ebenezer G J, O'Donnell R, Hauer P, Cimino N P, McArthur J C, Polydefkis M. Impaired neurovascular repair in subjects with diabetes following experimental intracutaneous axotomy. Brain. 2011; 134:1853-1863
4. Cameron N E, Cotter M A. Effects of antioxidants on nerve and vascular dysfunction in experimental diabetes. Diabetes Res Clin Pract. 1999; 45:137-146
5. Cameron N E, Gibson T M, Nangle M R, Cotter M A. Inhibitors of advanced glycation end product formation and neurovascular dysfunction in experimental diabetes. Ann N Y Acad Sci. 2005; 1043:784-792

6. Kusano K F, Allendoerfer K L, Munger W, Pola R, Bosch-Marce M, Kirchmair R, et al. Sonic hedgehog induces arteriogenesis in diabetic vasa nervorum and restores function in diabetic neuropathy. Arterioscler Thromb Vasc Biol. 2004; 24:2102-2107
7. Ii M, Nishimura H, Kusano K F, Qin G, Yoon Y S, Wecker A, et al. Neuronal nitric oxide synthase mediates statin-induced restoration of vasa nervorum and reversal of diabetic neuropathy. Circulation. 2005; 112:93-102
8. Schratzberger P, Walter D H, Rittig K, Bahlmann F H, Pola R, Curry C, et al. Reversal of experimental diabetic neuropathy by vegf gene transfer. J Clin Invest. 2001; 107:1083-1092
9. Goldstein A L, Slater F D, White A. Preparation, assay, and partial purification of a thymic lymphocytopoietic factor (thymosin). Proc Natl Acad Sci USA. 1966; 56:1010-1017
10. Smart N, Risebro C A, Melville A A, Moses K, Schwartz R J, Chien K R, et al. Thymosin beta4 induces adult epicardial progenitor mobilization and neovascularization. Nature. 2007; 445:177-182
11. Crockford D. Development of thymosin beta4 for treatment of patients with ischemic heart disease. Ann N Y Acad Sci. 2007; 1112:385-395
12. ClinicalTrials.gov. http://clinicaltrials.gov/ct2/show/NCT01311518
13. Morris D C, Chopp M, Zhang L, Lu M, Zhang Z G. Thymosin beta4 improves functional neurological outcome in a rat model of embolic stroke. Neuroscience. 2010; 169:674-682
14. Xiong Y, Mahmood A, Meng Y, Zhang Y, Zhang Z G, Morris D C, et al. Treatment of traumatic brain injury with thymosin beta in rats. J Neurosurg. 2011; 114:102-115
15. Zhang J, Zhang Z G, Morris D, Li Y, Roberts C, Elias S B, et al. Neurological functional recovery after thymosin beta4 treatment in mice with experimental auto encephalomyelitis. Neuroscience. 2009; 164:1887-1893
16. Philp D, Badamchian M, Scheremeta B, Nguyen M, Goldstein A L, Kleinman H K. Thymosin beta 4 and a synthetic peptide containing its actin-binding domain promote dermal wound repair in db/db diabetic mice and in aged mice. Wound Repair Regen. 2003; 11:19-24
17. Suri C, Jones P F, Patan S, Bartunkova S, Maisonpierre P C, Davis S, et al. Requisite role of angiopoietin-1, a ligand for the tie2 receptor, during embryonic angiogenesis. Cell. 1996; 87:1171-1180
18. Teichert-Kuliszewska K, Maisonpierre P C, Jones N, Campbell A I, Master Z, Bendeck M P, et al. Biological action of angiopoietin-2 in a fibrin matrix model of angiogenesis is associated with activation of tie2. Cardiovasc Res. 2001; 49:659-670
19. Thebaud B, Ladha F, Michelakis E D, Sawicka M, Thurston G, Eaton F, et al. Vascular endothelial growth factor gene therapy increases survival, promotes lung angiogenesis, and prevents alveolar damage in hyperoxia-induced lung injury: Evidence that angiogenesis participates in alveolarization. Circulation. 2005; 112:2477-2486
20. Maisonpierre P C, Suri C, Jones P F, Bartunkova S, Wiegand S J, Radziejewski C, et al. Angiopoietin-2, a natural antagonist for tie2 that disrupts in vivo angiogenesis. Science. 1997; 277:55-60
21. Tuo Q H, Zeng H, Stinnett A, Aschner J L, Liao D F, et al. Critical role of angiopoietins/tie-2 in hyperglycemic exacerbation of myocardial infarction and impaired angiogenesis. Am J Physiol Heart Circ Physiol. 2008; 294:H2547-2557
22. Chen J X, Stinnett A. Disruption of ang-1/tie-2 signaling contributes to the impaired myocardial vascular maturation and angiogenesis in type ii diabetic mice. Arterioscler Thromb Vasc Biol. 2008; 28:1606-1613
23. Kim H W, Kim J L, Lee H K, Hur D Y, Yun I H, Kim S D. Enalapril alters expression of key growth factors in experimental diabetic retinopathy. Curr Eye Res. 2009; 34:976-987
24. Chen J X, Stinnett A. Ang-1 gene therapy inhibits hypoxia-inducible factor-1 alpha (hif-1 alpha)-prolyl-4-hydroxylase-2, stabilizes hif-1 alpha expression, and normalizes immature vasculature in db/db mice. Diabetes. 2008; 57:3335-3343
25. Rasul S, Reiter M H, Ilhan A, Lampichler K, Wagner L, Kautzky-Willer A. Circulating angiopoietin-2 and soluble tie-2 in type 2 diabetes mellitus: A cross-sectional study. Cardiovasc Diabetol. 2011; 10:55
26. Zhang Z, Zhang R L, Jiang Q, Raman S B, Cantwell L, Chopp M. A new rat model of thrombotic focal cerebral ischemia. J Cereb Blood Flow Metab. 1997; 17:123-135
27. Wang L, Chopp M, Szalad A, Liu Z, Bolz M, Alvarez F M, et al. Phosphodiesterase-5 is a therapeutic target for peripheral neuropathy in diabetic mice. Neuroscience. 2011; 193:399-410
28. Vanderah T W, Suenaga N M, Ossipov M H, Malan T P, Jr., Lai J, Porreca F. Tonic descending facilitation from the rostral ventromedial medulla mediates opioid-induced abnormal pain and antinociceptive tolerance. J Neurosci. 2001; 21:279-286
29. South S M, Smith M T. Apparent insensitivity of the hotplate latency test for detection of antinociception following intraperitoneal, intravenous or intracerebroventricular m6g administration to rats. J Pharmacol Exp Ther. 1998; 286:1326-1332
30. Zhang Z, Davies K, Prostak J, Fenstermacher J, Chopp M. Quantitation of microvascular plasma perfusion and neuronal microtubule-associated protein in ischemic mouse brain by laser-scanning confocal microscopy. J Cereb Blood Flow Metab. 1999; 19:68-78
31. Wu Q D, Wang J H, Fennessy F, Redmond H P, Bouchier-Hayes D. Taurine prevents high-glucose-induced human vascular endothelial cell apoptosis. Am J Physiol. 1999; 277:01229-1238
32. Kim H K, Kim Y J, Kim J T, Kwon C H, Kim Y K, Bae Y C, et al. Alterations in the proangiogenic functions of adipose tissue-derived stromal cells isolated from diabetic rats. Stem Cells Dev. 2008; 17:669-680
33. Perrone L, Peluso G, Melone M A. Rage recycles at the plasma membrane in s100b secretory vesicles and promotes schwann cells morphological changes. J Cell Physiol. 2008; 217:60-71
34. Lee O H, Kim Y M, Lee Y M, Moon E J, Lee D J, Kim J H, et al. Sphingosine 1-phosphate induces angiogenesis: Its angiogenic action and signaling mechanism in human umbilical vein endothelial cells. Biochem Biophys Res Commun. 1999; 264:743-750
35. Zhang R, Wang L, Zhang L, Chen J, Zhu Z, Zhang Z, et al. Nitric oxide enhances angiogenesis via the synthesis of vascular endothelial growth factor and cgmp after stroke in the rat. Circ Res. 2003; 92:308-313
36. Zhang R, Zhang Z, Wang L, Wang Y, Gousev A, Zhang L, et al. Activated neural stem cells contribute to stroke-induced neurogenesis and neuroblast migration toward the infarct boundary in adult rats. J Cereb Blood Flow Metab. 2004; 24:441-448
37. Wang L, Zhang Z, Wang Y, Zhang R, Chopp M. Treatment of stroke with erythropoietin enhances neurogenesis and angiogenesis and improves neurological function in rats. Stroke. 2004; 35:1732-1737
38. Wang L, Gang Zhang Z, Lan Zhang R, Chopp M. Activation of the pi3-k/akt pathway mediates cgmp enhanced-neurogenesis in the adult progenitor cells derived from the subventricular zone. J Cereb Blood Flow Metab. 2005; 25:1150-1158
39. Livak K J, Schmittgen T D. Analysis of relative gene expression data using real-time quantitative pcr and the 2(-delta delta c(t)) method. Methods. 2001; 25:402-408
40. Jeong J O, Kim M O, Kim H, Lee M Y, Kim S W, Ii M, et al. Dual angiogenic and neurotrophic effects of bone marrow-derived endothelial progenitor cells on diabetic neuropathy. Circulation. 2009; 119:699-708
41. Said G. Diabetic neuropathy—a review. Nat Clin Pract Neurol. 2007; 3:331-340
42. Tesfaye S, Boulton A J, Dyck P J, Freeman R, Horowitz M, Kempler P, et al. Diabetic neuropathies: Update on definitions, diagnostic criteria, estimation of severity, and treatments. Diabetes Care. 2010; 33:2285-2293
43. Pande M, Hur J, Hong Y, Backus C, Hayes J M, Oh S S, et al. Transcriptional profiling of diabetic neuropathy in the bks db/db mouse: A model of type 2 diabetes. Diabetes. 2011; 60:1981-1989
44. Grant D S, Kinsella J L, Kibbey M C, LaFlamme S, Burbelo P D, Goldstein A L, et al. Matrigel induces thymosin beta 4 gene in differentiating endothelial cells. J Cell Sci. 1995; 108 (Pt 12):3685-3694
45. Qiu F Y, Song X X, Zheng H, Zhao Y B, Fu G S. Thymosin beta4 induces endothelial progenitor cell migration via pi3k/akt/enos signal transduction pathway. J Cardiovasc Pharmacol. 2009; 53:209-214
46. Bock-Marquette I, Saxena A, White M D, Dimaio J M, Srivastava D. Thymosin beta4 activates integrin-linked kinase and promotes cardiac cell migration, survival and cardiac repair. Nature. 2004; 432:466-472
47. Smart N, Risebro C A, Melville A A, Moses K, Schwartz R J, Chien K R, et al. Thymosin beta-4 is essential for coronary vessel development and promotes neovascularization via adult epicardium. Ann N Y Acad Sci. 2007; 1112:171-188
48. Campana W M. Schwann cells: Activated peripheral glia and their role in neuropathic pain. Brain Behav Immun. 2007; 21:522-527
49. Sobue G. [the role of schwann cells in peripheral nerve degeneration and regeneration—ngf-ngf receptor system]. Rinsho Shinkeigaku. 1990; 30:1358-1360
50. Frostick S P, Yin Q, Kemp G J. Schwann cells, neurotrophic factors, and peripheral nerve regeneration. Microsurgery. 1998; 18:397-405

TABLES

TABLE 1

Effect of TB4 on bodyweight
Weight, g

| Groups | 0 w | 2 w | 4 w | 6 w | 8 w |
|---|---|---|---|---|---|
| dm-Saline | 30.3 ± 0.8* | 30.8 ± 0.7* | 30.4 ± 0.9* | 30.1 ± 0.7* | 30.9 ± 0.8* |
| db-Saline | 61.0 ± 0.8 | 61.2 ± 0.7 | 59.3 ± 1.2 | 57.6 ± 42.2 | 57.1 ± 2.8 |
| db-TB4 (6 mg/kg) | 59.5 ± 0.9 | 57.1 ± 1.1 | 56.2 ± 1.2 | 53.7 ± 1.5 | 53.0 ± 1.7 |
| db-TB4 (24 mg/kg) | 58.9 ± 1.1 | 58.1 ± 1.2 | 55.7 ± 1.5 | 56.0 ± 1.4 | 54.8 ± 1.6 |

Values are mean ± SE.
*P < 0.01 versus db + Saline group.
n = 10/group.
W = week,
0 w represents before the treatment, while other numbers indicate after the treatment.
dm = db/m mouse;
db = db/db mouse.

TABLE 2

Effect of TB4 on blood glucose
Blood glucose (g/dl)

| Groups | 0 w | 2 w | 4 w | 6 w | 8 w |
|---|---|---|---|---|---|
| dm-Saline | 141.6 ± 14.5* | 138.6 ± 6.4* | 141.4 ± 7.7* | 140.1 ± 8.0* | 141.3 ± 4.6* |
| db-Saline | 513.8 ± 14.0 | 516.6 ± 18.6 | 517.6 ± 10.7 | 516.4 ± 32.3 | 524.2 ± 23.3 |
| db-TB4 (6 mg/kg) | 503.4 ± 24.0 | 513.4 ± 17.5 | 512.8 ± 24.8 | 517.6 ± 21.4 | 503.3 ± 18.0 |
| db-TB4 (24 mg/kg) | 517.6 ± 15.0 | 515.9 ± 13.1 | 504.7 ± 16.5 | 521.6 ± 16.0 | 515.8 ± 19.3 |

Values are mean ± SE.
*P < 0.01 versus db + Saline group.
n = 10/group.
W = week,
0 w represents before the treatment, while other numbers indicate after the treatment.
dm = db/m mouse;
db = db/db mouse.

What is claimed is:

1. A method of treatment for promoting recovery of peripheral neuropathy in a subject, comprising administering to a subject in need of such treatment a therapeutically effective amount of a composition comprising a peptide comprising an amino acid sequence of SEQ ID NO: 1, SEQ ID NO: 3, and/or SEQ ID NO: 4.

2. The method of claim 1 wherein said neuropathy is associated with diabetes in said subject.

3. The method of claim 1 wherein said diabetes is diabetes mellitus.

4. The method of claim 1 wherein said composition is administered to said subject at a dosage within a range of about 1-100 micrograms of the peptide of the composition comprising SEQ ID NO: 1, SEQ ID NO: 3, and/or SEQ ID NO: 4.

5. The method of claim 1 wherein said composition is administered by direct administration to said subject's tissue, or by intravenous, intraperitoneal, intramuscular, subcutaneous, inhalation, transdermal or oral administration, to said subject.

6. The method of claim 1 wherein said composition is administered systemically.

7. The method of claim 1 wherein said composition is in the form of a solution, gel, creme, paste, lotion, spray, suspension, dispersion, salve, hydrogel or ointment formulation.

8. The method of claim 1 wherein any of said peptides comprises a recombinant or synthetic peptide.

\* \* \* \* \*